United States Patent [19]
Sims et al.

[11] Patent Number: 5,453,366
[45] Date of Patent: Sep. 26, 1995

[54] METHOD OF CLONING BOVINE EMBRYOS

[76] Inventors: Michele M. Sims, 10955 FM 3356, Anna, Tex. 75409; Charles F. Rosenkrans, Jr., 3169 Misa, Fayetteville, Ark. 72703

[21] Appl. No.: 31,815

[22] Filed: Mar. 15, 1993

Related U.S. Application Data

[63] Continuation-in-part of Ser. No. 606,418, Oct. 31, 1990, abandoned, which is a continuation-in-part of Ser. No. 558,969, Jul. 26, 1990, Pat. No.5,096,822.

[51] Int. Cl.$^6$ .............................. C12N 15/00; C12N 5/00
[52] U.S. Cl. .................................. 435/172.3; 435/240.1; 435/240.2; 800/2; 800/DIG. 4; 800/DIG. 6
[58] Field of Search .............................. 800/2; 435/172.3

[56] References Cited

U.S. PATENT DOCUMENTS

| | | |
|---|---|---|
| 4,994,384 | 2/1991 | Prather et al. . |
| 5,057,420 | 10/1991 | Massey . |
| 5,096,822 | 3/1992 | Rosenkrans . |

OTHER PUBLICATIONS

Bavister et al., 1983, "Development of Preimplantation Embryos of the Golden Hamster in a Defined Culture Medium, " Biol. Reprod., 28:235.
Bondioli, K. R. et a.. 1990, "Production of Identical Bovine Offspring by Nuclear Transfer," Theriogenology, vol. 13(1):165–174.
Briggs and King, 1952, "Transplantation of Living Nuclei from Blastula Cells into Enucleated Frogs' Eggs, " Zoology 38:455–463.
Briggs, R., et al., 1964, "Transplantation of Nuclei of Various Cell Types from Neurulae of the Mexican Axolotl (Ambystoma mexicanum)," Develop. Biol. 10:233.
Comandon and de Fonbrune, 1939, "Greffe Nucleaire Totale, Simple ou Multiple, Chez une Amibe," Soc. Biol. 130:744.
Critzer, E. S. and N. L. First, 1986, "Use of Flourescent Stain for Visualization of Nuclear Material in Living Oocytes and Early Embryos," Stain Technology, 61(1) :1–5.
Eyestone, et al., 1987, "Culture of One–and Two–Cell Bovine Embryos to the Blastocyst Stage in the Ovine Oviduct", Theriogenology, 28:1–7.
Elsdale et al., 1960, "A Description of the Technique for Nuclear Transplantation in Xenopus laevis," J. Embryol. Exp. Morph., 8(4):437–444.
First and Prather, 1991, "Genomic Potential in Mammals," Diffeerentiation, 48:1–8.
Graham, C. F., 1969, "The Fusion of Cells with One and Two Cell Mouse Embryos," Wistar Inot. Symp. Monogr., 9:19.
Illmensee, K. and P. C. Hoppe, 1981, "Nuclear Transplantation in Mus musculus: Development Potential of Nuclei from Preimplantation Embryos," Cell 23:9.
Kono, T., et al., 1991, "Development of Enucleated Mouse Oocytes Reconstituted with Embryonic Nuclei," J. Reprod. Fert., 93:165–172.
McGrath, J. and D. Solter, 1983, "Nuclear Transplantation in the Mouse Embryo by Microsurgery and Cell Fusion," Science, 220:1300.
McGrath, J. and D. Solter, 1984, "Inability of Mouse Blastomere Nuclei Transferred to Enucleated Zygotes to Support Development In Vitro," Science, 226:1317–1319, 1984.
Navara, C. S. et al., 1992, "Timing of Polarization in Bovine Embryos and Developmental Potential of Polarized Blastomeres," (Abstract) Proc. Soc. Study Reprod., North Carolina State University (Jul. 12–15, 1992), p. 71.
Parrish, J. J. et al., 1988, "Capacitation of Bovine Sperm by Heparin," Biol. Reprod. 38, 1171–1180.
Prather, R. S. et al., 1987, Biol. Reprod., 37:859–866.
Prather, R. S. et al., 1989, Biol. Reprod., 41:414–418.
Robl, J. M. et al., 1986, "Nuclear Transplantation in Mouse Embryos: Assessment of Recipient Cell Stage," Biol. Reprod., 34:733–739.
Sirard et al., 1988, Biol. Reprod., 39:546–552.
Smith, L. C. and I. Wilmut, 1989, "Influence of Nuclear and Cytoplasmic Activity on the Development in vivo of Sheep Embryos after Nuclear Transplantation," Biol. Reprod., 40:1027–1035.
Stice, S. L., and J. M. Robl, 1988, Biol. Reprod., 39:657–664.
Surani, M.A.H. et al., 1986, "Nuclear Transplantation in the Mouse: Heritable Differences Between Paternal Genomes after Activation ofthe Embryonic Genome." Cell, 45:127–136.
Tsunoda, Y. et al., 1987, J. Exp. Zool., (242:147–151).
Willadsen, S. M., 1986, Nature, 320:63–65.

Primary Examiner—Jacqueline Stone
Assistant Examiner—Deborah Crouch
Attorney, Agent, or Firm—Dewitt Ross & Stevens

[57] ABSTRACT

An improved method of cloning mammalian embryos by transferring a nucleus from a donor mammalian embryo to an enucleated recipient oocyte and culturing the nuclear transferred bovine embryo in vitro is described. The improvement includes positioning the donor embryo nucleus adjacent to the enucleated recipient oocyte, and maintaining the nucleus and oocyte in a maintenance medium for a time sufficient to mature the cytoplasm of the enucleated recipient oocyte prior to fusing the donor nucleus to the recipient oocyte.

3 Claims, No Drawings

METHOD OF CLONING BOVINE EMBRYOS

REFERENCE TO RELATED APPLICATION

This is a continuation-in-part of U.S. Ser. No 07/606,418, filed on Oct. 31, 1990, entitled "METHOD OF CLONING MAMMALIAN EMBRYOS," abandoned which is a continuation-in-part of Ser. No. 558,969 filed Jul. 26, 1990 now U.S. Pat. No. 5,096,822, which application and patent are incorporated herein by reference.

FIELD OF THE INVENTION

The present invention is generally directed to an improved method for cloning or multiplying mammalian embryos and to an improved method for transferring the nuclei of donor embryos into enucleated recipient oocytes, that is, oocytes from which the nuclei have been removed. The present invention is specifically directed to enhancing mammalian embryo development after nuclear transfer by including a maintenance period prior to fusion which promoted increased inner cell mass surface area contact.

DESCRIPTION OF THE PRIOR ART

Advanced genetic improvement and selection techniques continue to be sought in the field of animal husbandry. With specific reference to dairy cattle, for example, significant increases in milk production have been made with the wide scale use of genetically superior sires and artificial insemination. Dairy cows today produce nearly twice as much milk as they did 30 years ago. Further genetic improvement can be accomplished by the multiplication of superior or genetically manipulated embryos by cloning.

It has now become an accepted practice to transplant embryos in cattle to aid in the production of genetically superior stock. The cloning of embryos together with the ability to transplant the cloned embryos makes it possible to produce multiple genetically identical animals. Embryo cloning is the process of transferring the nucleus of an embryonic donor cell to an enucleated recipient ovum or oocyte. The clone then develops into a genetically identical offspring to the donor embryo.

Nuclear transfer was first accomplished in *Amoeba sphaeronucleus* in 1939 by Comandon and de Fonbrune. This was followed in 1952 by successful nuclear transfer in *Rana pipiens* by Briggs and King. The procedure for successful nuclear transfers, according to Briggs and King (1952), included the following:

1) activation of a recipient oocyte:

2) enucleation, i.e., the process of removing or inactivating the chromosomes from the recipient oocyte; and 3) transfer of a whole blastomere (a cell resulting from embryo cleavage prior to gastrulation) with a nucleus, from a blastula or early gastrula stage embryo back to the enucleated oocyte.

Embryo cloning has now been successfully performed in cattle, sheep, rabbits, pigs and mice (Prather, et al., 1987; Willadsen, 1986; *Stice and Robl*, 1989; *Prather, et al.*, 1989; *Tsunoda, et al.*, 1987).

Elsdale, et al. (1960) utilized ultraviolet irradiation to, in one step, inactivate the egg pronucleus and activate the unfertilized oocyte. In the axolotl, activation was reported by electrical shock with chromosomes of the egg nucleus being eliminated by ultraviolet irradiation, (Briggs, et al., 1964). Transfer of a whole blastomere containing a nucleus into the enucleated oocyte via a small bore micropipette was the common method of nuclear transfer for all these techniques.

Two techniques have been used for nuclear transfer in the mouse. Illmensee and Hoppe (1981) used a totally surgical method in which a micropipette was inserted through the plasma membrane and into the cytoplasm of a pronuclear stage embryo for pronuclear removal and subsequent insertion of donor nuclei. McGrath and Solter (1983) reported a nondisruptive method of transplanting nuclei. Nuclei were removed as membrane bounded pronuclear karyoplasts without penetrating the plasma membrane of the embryo. The nucleus was inserted into a recipient cell by cell fusion, using Sendai virus as the fusigenic agent. A small volume of Sendai virus suspension was aspirated after removal of the donor nucleus and the virus suspension and the pronuclear karyoplasts were injected sequentially into the perivitelline space of the recipient embryo. At best, the microsurgical method of Illmensee and Hoppe (1981) was about 30–40% efficient, whereas the nondisruptive method of McGrath and Solter (1983) was greater than 90% efficient. These techniques have been successful in producing blastocyst stage embryos which do not continue development to term. Reports that Illmensee and Hoppe produced three live mice have been questioned.

It was later reported that blastocyst stage embryos and mice were produced by transferring nuclei into enucleated pronuclear zygotes only when the donor cell stage was also pronuclear or at a very early two-cell stage (McGrath and Solter, 1984; Surani, et al., 1986; and Robl, et al., 1986).

While cloning procedures have been successful for a variety of species, the embryo development after nuclear transfer is lower than non-manipulated contemporaries (Bondioli, et al. 1990).

Embryo development after nuclear transfer has been improved by various procedures involving arresting the embryo cytoskeleton with a cytochalasin B culture during cell fusion. Cytochalasin causes the embryo cytoskeleton to become more elastic, making the embryo more conducive to cell fusion (McGrath and Solter, 1983). It is believed that periods of cytoskeletal repair before cell fusion may increase subsequent embryo development.

SUMMARY OF THE INVENTION

The present invention is directed to a technique which improves known methods of producing cloned mammalian embryos by transferring a nucleus from a donor embryo to a recipient oocyte. The improved cloning method includes isolating a donor membrane-bounded nucleus from a cell of a donor embryo, removing the nuclear chromosomal material from an oocyte to create an enucleated recipient oocyte, maintaining the donor membrane-bounded nucleus and the enucleated recipient oocyte for a period of time sufficient to increase inner cell mass surface area contact between the donor membrane-bounded nucleus and the enucleated recipient oocyte, and fusing the membranes of the donor membrane-bounded nucleus and the enucleated recipient oocyte together to form an embryonic single cell with a nucleus from the donor embryo, referred to herein as a "nuclear transfer embryo" or an "NT". The improvement in this invention lies in the maintenance period prior to fusion.

The present invention is more specifically directed to a method of transferring a donor membrane-bounded nucleus isolated from a donor bovine embryo, the embryo being at a stage of development where significant cell differentiation has not occurred, to a recipient metaphase II bovine oocyte and culturing the nuclear transferred embryo in vitro. The method comprises removing the nuclear chromosomal material from an oocyte to form an enucleated recipient oocyte; maintaining the donor membrane-bounded nucleus and the enucleated recipient oocyte in a maintenance medium for a period of time sufficient to mature the cytoplasm, such that the matured cytoplasm enables the oocyte to advance the nucleus directly into cleavage without decondensing or recondensing the chromatin matter in the cytoplasm; and fusing the membranes of the donor membrane-bounded nucleus and the enucleated recipient oocyte together to form an embryonic single cell with a nucleus from the donor embryo.

The present invention is also directed to a method for producing cloned mammalian embryos. The method comprises removing the nuclear chromosomal material from a metaphase II bovine oocyte to form an enucleated recipient oocyte; maintaining the enucleated recipient oocyte in a maintenance medium for a period of time sufficient to mature the cytoplasm, such that the matured cytoplasm enables the oocyte to advance the nucleus directly into cleavage without decondensing or recondensing the chromatin matter in the cytoplasm; and inducing cell fusion between the membranes of the donor membrane-bounded nucleus and the enucleated recipient oocyte to form an embryonic single cell with a nucleus from the donor.

The present invention is further directed to an improved method for producing cloned mammalian embryos by transferring a donor membrane-bounded nucleus isolated from a donor bovine embryo, the embryo being at a stage of development where significant cell differentiation has not occurred, to an enucleated recipient metaphase II bovine oocyte and culturing the nuclear transfer embryo in vitro. The improvement comprises maintaining the enucleated recipient oocyte in a maintenance medium for a period of time sufficient to activate the cytoplasm, such that the activated cytoplasm enables the oocyte to advance the nucleus directly into cleavage without decondensing or recondensing the chromatin matter in the cytoplasm.

Further still, the present invention is directed to a method of transferring a donor membrane-bounded nucleus isolated from a donor bovine embryo, the embryo being at a stage of development where significant cell differentiation has not occurred, to a recipient metaphase II bovine oocyte and culturing the nuclear transferred embryo in vitro. The method comprises removing the nuclear chromosomal material from an oocyte to form an enucleated recipient oocyte; maintaining the enucleated recipient oocyte in a maintenance medium for approximately 6–28 hours prior to fusing the cell membranes; and fusing the membranes of the donor membrane-bounded nucleus and the enucleated recipient oocyte together to form an embryonic single cell with a nucleus from the donor embryo.

By maintaining the nucleus of the membrane-bounded donor embryo and the enucleated recipient oocyte in a maintenance medium for an elongated period of time, typically 24–52 hours after oocyte aspiration from ovarian follicles, the nucleus and oocyte undergo a physiological change which enhances the ability of each of the membranes to fuse. This results in increased fusion and developmental rates.

Further objects, features and advantages of the present invention will be apparent from the following detailed description and appended claims.

REFERENCE TO CITATIONS

A full citation of the references cited in this disclosure is found in the Bibliography preceding the claims.

DETAILED DESCRIPTION OF THE INVENTION

The present invention is directed to an improvement in the series of steps which collectively result in the cloning of mammalian embryos by nuclear transplantation. Although it is contemplated that the embryo cloning procedure of the present invention may be utilized on a variety of mammals, the procedure will be described with reference to the bovine species. However, the present invention does not restrict the cloning procedure to bovine embryos.

The cloning procedure includes a non-disruptive method of removing the nucleus from a mature recipient oocyte and isolating a nucleus from a donor embryo, bounded by a membrane, either by removal of the nucleus from the donor embryo or by isolating a blastomere itself. The nucleus is then positioned so it is adjacent to the recipient oocyte and the nucleus is fused with the recipient cell to form an embryonic single cell.

The standard embryo cloning process follows a basic six step procedure:

1) selecting a proper recipient oocyte and a multicellular embryo donor for nuclear transfer;

2) isolating a blastomere from the donor;

3) enucleating, i.e., removing the nuclear material from the recipient oocyte;

4) introducing the membrane-bounded nucleus of the blastomere adjacent to the enucleated recipient oocyte;

5) orienting the nucleus and the recipient oocyte for cell fusion; and 6) fusing the membrane surrounding the nucleus to the membrane of the recipient oocyte and activating the recipient oocyte by dielectrophoresis, The overall procedure disclosed herein may be described as cloning or as multiplication of embryos by nuclear transfer followed by a prolonged maintenance period to increase fusion and developmental rates of multiple genetically identical embryos, and ultimately, animals.

Donor Cell Embryos

The donor embryos may be obtained by flushing from surgically recovered oviducts or may be nonsurgically flushed from the uterus in manners known to the art.

Preferred donor embryos generally have a development of from 2 to 64 cells. In domestic animals such as cattle, an embryo at the 32-cell stage is called a morula. At this stage, the cells become more compacted together. After the morula stage, an internal inner cell mass space enlarges to create a central fluid-filled cavity known as the blastocoel. At this stage, the embryo is known as a blastocyst. The cells of the blastocyst form a spherical shell having an outer cell layer known as the trophectoderm. One pole of the blastocyst is distinguished by a thicker accumulation of cells, known as the inner cell mass (ICM), inside the trophectoderm. The embryo is derived from the ICM, while the cells of the trophectoderm are the precursor of extraembryonic tissues and the placenta. Reference is made to Navara et al. (1992) for a more detailed description of this development.

Donor embryos at the blastocyst stage of development can be used for cloning as long as significant cell differentiation has not occurred. In the ICM of a later stage embryo, for example, the cells may remain totipotent; that is, they may not have undergone significant cellular differentiation, whereas the outer cells have differentiated to form the trophectoderm and are not suitable for use in embryonic cloning processes (Navara et al., 1992).

For the morula stage, i.e., 32–60-cell stage, Navara et al. (1992) showed totipotency in nonpolarized cells, but not in polarized cells. Polarization is the first evidence of commitment to cellular differentiation for the first differentiation event. The polarized cells are identified by membrane staining of the microvilli surrounding the cells. ICM cells do not always have microvilli around them, but the cleaving stages do. At the cleaving stages, if the microvilli are stained entirely around the cell, then the cells are not polarized. If the microvilli have patches of stain missing, they are polarized.

The cells of the ICM are known as embryonic stem (ES) cells because they have the ability to proliferate in an undifferentiated state, as well as give rise to differentiated products. The isolation and multiplication in culture of totipotent embryonic stem cells have value in providing a large population of identical cells for use by nuclear transfer to produce clonal offspring (First and Prather, 1991). Nuclear transfer of nuclei from murine ICM into enucleated oocytes was performed by Illmensee and Hoppe (1981) and Kono et al. (1991) with limited success. Smith and Wilmut (1989) disclosed the production of sheep embryo by electrofusion-mediated nuclear transplantation in which uncultured single cells derived from the ICM of early blastocyst stage embryos were fused to unfertilized enucleated secondary oocytes.

In bovine embryo nuclear transfer processes, donor cells from the 2-cell stage through the inner cell mass stage of the blastocyst have been shown to be totipotent. This includes cultured cells of the inner cell mass.

Methods of in vitro maturation, fertilization and development also can be used to generate donor embryos. Donor embryos at the 16–64 cell stage are sometimes referred to as morula rather than blastula. Nevertheless, for convenience the term blastula will be used herein to refer to the embryo, regardless of age, and the term blastomere will be used to refer to a single cell from any such embryo.

The nucleus of the donor embryo should be membrane-bounded to be used optimally in the procedure. Such a membrane-bounded nucleus may either consist of an entire blastomere or may consist of a karyoplast, which is an aspirated cellular subset including a nucleus and a small amount of cytoplasm bounded by a plasma membrane.

Micromanipulation of the embryos is performed in a manner similar to the methods of McGrath and Solter (1983), which is incorporated herein for details of the micromanipulation technique. Micromanipulation is performed using a cell holding pipette, having an outer diameter of about 120 to 180 micrometers and an inner diameter of approximately 25 to 35 micrometers, and a beveled, sharpened enucleation and transfer pipette having an outer diameter of approximately 10 to 45 micrometers, depending upon the size of the blastomere.

The donor embryos may optionally be treated with cytochalasin B. The nuclei of the donor embryos are prepared for transfer either by aspirating a part of the blastomere which contains the nucleus, thus creating a karyoplast, or by aspirating the entire blastomere. Aspirating the entire blastomere is preferred.

Culture and Maintenance Media

There are a variety of embryo culture and maintenance media routinely used for the collection of embryos, and specifically bovine embryos. Examples of known media, which may be used for bovine embryo culture and maintenance, include Ham's F-10+10% fetal calf serum, Tissue Culture Medium-199 (TCM 199)+10% fetal calf serum, Tyrodes's-Albumin-Lactate-Pyruvate, Dulbecco's Phosphate Buffered Saline, Eagle's and Whitten's media. One of the most common media for the collection and freezing of embryos is Dulbecco's Phosphate Buffered Saline (PBS) incorporating 1 to 20% fetal calf serum, new born serum or steer serum. If the embryos are to be kept in an embryo culture medium for a substantial period of time, the PBS is normally supplemented with 10 to 20% serum.

Eyestone, et al. (1987) reported that ligated ovine oviducts would support development of bovine embryos from the 1-cell to blastocyst stage. Pregnancies and live calves were produced after transfer of cultured embryos to recipient heifers. Cultures of 1- and 2-cell embryos in the oviducts of intact cycling, ovariectomized or anestrous ewes produced morphologically normal morulae and blastocysts followed by pregnancies in recipient heifers, suggesting that ovarian activity was not required for normal embryo development in the oviduct.

Another embryo culture and maintenance medium is described in parent U.S. Pat. No. 5,096,822 to Rosenkrans, Jr. et al., entitled "Bovine Embryo Medium," which is incorporated herein by reference. This embryo medium, named CR1, comprises a culture solution containing the nutritional substances necessary to support an embryo and is the preferred maintenance medium for use with this invention. The medium contains hemicalcium L-lactate in amounts ranging from 1.0 mM to 10 mM, preferably 1.0 mM to 5.0 mM. Hemicalcium L-lactate is L-lactate with a hemicalcium salt incorporated thereon. Hemicalcium L-lactate is significant in that a single component satisfies two major requirements in the culture medium: 1) the calcium requirement necessary for compaction and cytoskeleton arrangement; and 2) the lactate requirement necessary for metabolism and electron transport. Hemicalcium L-lactate also serves as valuable mineral and energy source for the medium necessary for viability of the embryos.

Advantageously, CR1 medium does not contain serum, such as fetal calf serum, and does not require the use of a co-culture of animal cells or other biological media, i.e, media comprising animal cells, e.g., oviductal cells. Biological media can sometimes be disadvantageous in that they may contain trace factors which may be harmful to the embryos and which are difficult to detect, characterize and eliminate.

Examples of the main components in CR1 medium include hemicalcium L-lactate, sodium chloride, potassium chloride, sodium bicarbonate and a minor amount of fatty-acid free bovine serum albumin. Additionally, a defined quantity of essential and non-essential amino acids may be added to the medium.

Salts are added to the medium to maintain a proper osmotic pressure or osmolarity of the medium. The preferred osmotic pressure is 265 milli-osmoles (mOSM). The concentration of salt generally ranges from 0 Mm to 155 Mm, preferably 110 mM to 115 mM. Examples of salts include sodium chloride and potassium chloride, preferably sodium chloride.

The fatty-acid free BSA is added as a surfactant, i.e., to prevent the embryos from adhering to each other. Unlike culture media known to the art, the CR1 medium requires only a minimal amount of the fatty-acid free BSA. The fatty-acid free BSA is added in amounts ranging from 1 mg/ml to 6 mg/ml, preferably 1 mg/ml to 3 mg/ml, and most preferably 3.0 mg/ml. Antibiotically effective amounts of an agent, such as gentamicin sulfate, penicillin, streptomycin, fungizone or other antibiotics, known to the art, can also be added. Additionally, a cryopreservation agent, known to the art, may be added to protect the cellular integrity of the bovine embryo during freezing operations. Further, chemical buffers, such as HEPES, may by added to maintain the proper pH in the absence of $CO_2$.

CR1 medium preferably contains the following components in the following quantities:

| | |
|---|---|
| sodium chloride | 114.7 mM |
| potassium chloride | 3.1 mM |
| sodium bicarbonate | 26.2 mM |
| hemicalcium L-lactate | 5 mm |
| fatty-acid free BSA | 3 mg/ml |

Oocyte

The "oocyte," as used here for the recipient oocyte, means an oocyte which develops from an oogonium and, following meiosis, becomes a mature ovum. It has been found that not all oocytes are equally optimal cells for efficient nuclear transplantation in mammals. For purposes of the present invention, metaphase II stage oocytes, matured either in vivo or in vitro, have been found to be optimal. Mature metaphase II oocytes may be collected surgically from either nonsuperovulated or superovulated cows or heifers 35 to 48 hours past the onset of estrus or past an injection of human Chorionic Gonadotrophin (hCG) or similar hormone. Alternatively, immature oocytes may be recovered by aspiration from ovarian follicles obtained from slaughtered cows or heifers and then may be matured in vitro in a maturation medium by appropriate hormonal treatment and culturing. As stated above, the oocyte is allowed to mature in a known maturation medium until the oocyte enters the metaphase II stage, generally 18–24 hours post aspiration. For purposes of the present invention, this period of time is known as the "maturation period." As used herein for calculation of time periods, "aspiration" refers to aspiration of the immature oocytes from ovarian follicles.

Mature oocytes can be first treated with cytochalasin B at about 7.5 micrograms per milliliter, or an effectively similar microtubal inhibitor at a concentration sufficient to allow the enucleation and transfer pipette to be inserted through the zona pellucida to allow for removal of a portion of the cytoplasm without, at any point, actually rupturing the plasma membrane. The mature oocyte is first held in place by mild suction by the cell holding pipette. The enucleation and transfer pipette is then inserted through the zona pellucida of the oocyte at the point of either the metaphase II bulge or adjacent to the first polar body, i.e., in a location intended to be adjacent to the metaphase chromosomes. The pipette does not penetrate the plasma membrane. Aspiration applied through the pipette draws a portion of the cytoplasm into the pipette which includes, in the case of the metaphase II bulge, the entire bulge surrounding cytoplasm, or, in the case of the first polar body, the cytoplasm adjacent to the polar body. This process is intended to draw all the metaphase chromosomes into the pipette. As the pipette is withdrawn, with suction maintained, the plasma membrane is stretched and then seals itself leaving a competent plasma membrane on the enucleated oocyte.

Maintenance Period

Prior to fusing the membranes of the donor membrane-bounded nucleus and the enucleated recipient oocyte together, it has been found that maintaining the nucleus and the oocyte together in the embryo maintenance medium significantly improves the development of the embryo post fusion. The enucleated oocyte is allowed to remain in the maintenance medium for a period of time sufficient to activate the cytoplasm, such that the activated cytoplasm enables the oocyte to advance the nucleus directly into cleavage without decondensing or recondensing the chromatin matter in the cytoplasm. The period is generally about 6–28 hours, preferably about 10–18 hours, after the oocyte maturation period to align the oocyte adjacent the membrane of the nucleus. Calculated from oocyte aspiration, the maintenance period will be about 24–52 hours, preferably 28–42 hours, post aspiration.

It was originally believed that the maintenance period increased the inner cell mass surface area contact area between the nucleus and the oocyte It is now known that the enucleated recipient oocyte should be maintained in the maintenance medium for a period of time sufficient to mature the cytoplasm in the oocyte, such that the matured state of the cytoplasm enables the oocyte to advance the nucleus of the donor embryo directly into cleavage without decondensing or recondensing the chromatin matte in the cytoplasm, after the nucleus has fused to the recipient oocyte. Processing the donor nucleus is affected by both age and enucleation status of the recipient oocyte.

The nucleus does not need to be in the maintenance medium during this time. The recipient oocyte should, however, be allowed to remain the maintenance medium for a period of time sufficient to mature the cytoplasm. Maturation of the cytoplasm reduces the activity of the cytoplasm. Thus, the presence of the oocyte in the medium will not prematurely decondense and recondense chromatin material in the nucleus and the fused cell will progress to nuclear division.

The transfer pipette, carrying the aspirated membrane-bounded nucleus, is inserted through the zona pellucida of the recipient enucleated oocyte; and the membrane-bounded nucleus is deposited under the zona pellucida with its membrane abutting the plasma membrane of the recipient oocyte.

Fusion of the Nucleus and the Oocyte

At approximately 24–52 hours, preferably 28–42 hours post aspiration or, stated differently, 6–28 hours, preferably 10–18 hours, after the nucleus is positioned such that its membrane is adjacent the enucleated oocyte, the cell surface contact appears to be at its peak. It is on this basis that membrane fusion may be enhanced with the use of the maintenance period of this invention.

Cell Fusion

A variety of fusion techniques may be employed for this invention. For example, the onset of the electricity by electrofusion can induce the fusion process. Electrofusion is accomplished by providing a pulse of electricity that is sufficient to cause a transient breakdown of the plasma membrane. This breakdown of the plasma membrane is very short and the membrane reforms very rapidly. If two adjacent membranes are induced to breakdown and upon reformation the lipid bilayers intermingle, small channels will open between the two cells. Due to the thermodynamic instability of such a small opening, it enlarges until the two cells become one. Reference is made to U.S. Pat. No. 4,994,384 to Prather et al., which is incorporated herein by reference, for a further discussion of this process. A variety of electrofusion media can be used including sucrose, mannitol, sorbitol and phosphate buffer solution.

Fusion can also be accomplished using Sendai virus as a fusigenic agent (Graham, 1969).

Polyethylene glycol (PEG) may also be used as a fusigenic agent. Under prescribed conditions, PEG provides excellent fusion results. In one protocol, the cells are fused in PEG (molecular weight 1,300–1,600 Sigma), which is mixed in a solution containing TL Hepes (approximately 1:0.25 µg/ml) and polyvinyl alcohol (PVA) (approximately 1 µg/ml), $CA^{2+}$ and $MG^{2+}$-free. The media containing the cells is then passed through one or more dilutions (approximately 1:1) of the above-described PEG media. The cell media is then allowed to rest in a culture media, such as TL Hepes containing fetal calf serum until the cell membranes return to a normal appearance. To activate the embryos, the embryos are washed in $CA^{2+}$ and $MG^{2+}$-free TL Hepes and exposed to an ionophore, for example, Ionomycin (Calbiochem). This is followed by another rest in TL Hepes containing fetal calf serum, after which the embryos are returned to a maturation medium for further maturation. Experimental conditions will vary depending upon the products used.

The techniques incorporated herein proved to be successful in producing blastocysts that, when transferred to cattle, were capable of establishing pregnancies.

In the preferred embodiment, fusion of the membrane-bounded nucleus with the enucleated recipient oocyte and simultaneous activation of the recipient oocyte are carried out by a single dielectrophoresis step using commercially available electrofusion equipment which is described below. Prior to electrofusing the donor embryo nucleus and enucleated recipient oocyte together, it is necessary to orient the cell membranes in the electric field. The term "orientation" as used herein is defined as the placement of the two cells such that the plane of contact of the two membranes, i.e., the plasma membrane of the body carrying the donor nucleus and the plasma membrane of the recipient oocyte, which will become fused together, is perpendicular to the electrical field. It has been found that random orientation results in a marked reduction in the successful fusion rate. If cells are oriented such that the fusion membranes are parallel, or at approximately a 45° angle, to the electrical field, the rate of successful fusion will decrease. The alignment may be done electrically or mechanically. If the size of the two cells is not greatly disproportionate, a small alignment alternating-current voltage (~5 volts per millimeter at 1000 KHz) for a short time (10 seconds) will cause the cells to reorient with their membranes apposed. Repeated pulses may be needed. If the cells vary greatly in size, mechanical manipulation may be required to properly orient the membranes.

The actual incorporation of a donor nucleus into an enucleated oocyte is conducted by a dielectrophoretic method of cell fusion, using a DC current and using a non-conductive, i.e., non-ionic, media such as a mannitol solution, sorbitol or sucrose (Zimmerman) based cell fusion media. The fusion phenomenon is the result of cell membrane breakdown and pore formation between properly oriented opposing cells. The pores, or small channels, created between the two cells are thermodynamically unstable because of the high surface curvature of the channels and the associated high tension in the membrane. This instability causes the channels to merge and enlarge until the membranes form a single cell which contains the nucleus from the donor embryo cell.

Fusion can be detected by staining techniques known to the art, for example the Hoechst staining procedure (Critzer (1986), or by visual inspection.

Post-Fusion Culture

The embryonic single-cell clones produced as described herein preferably are cultured, either in vitro or in vivo, to the morula or blastula stage. For example, the clones may be cultured in the oviduct of sheep, or other suitable animal, or in a suitable culture medium. The embryos then may be transplanted into the uteri of cattle at a suitable stage of the estrous cycle. The procedures for transplantation are commonly known and practiced in the embryo transfer field. A percentage of these transplants will initiate pregnancies in the maternal surrogates. Animals born of these pregnancies will be genetically identical where the donor cells were from a single embryo or a clone thereof.

The following example is offered by way of illustration and not by way of limitation.

EXPERIMENTAL PROCEDURES

Source of Recipient Oocytes and Donor Embryos. The oocyte-cumulus complexes (OCC) were aspirated from bovine ovaries recovered from a slaughterhouse in Milwaukee, Wis. The ovaries were transported from the slaughterhouse to the laboratory in insulated containers with saline (0.9%; 30°±2° C.). After arrival, the ovaries were washed with 30° C. water and placed into a flask containing fresh saline (0.9%) in a water bath maintained at 30° C. Follicular contents were harvested by aspiration using an 18-gauge needle and accumulated in a 50 ml sterile conical tube (Falcon #2070). Following aspiration, OCC were located using 100 mm plates in a warm room (30°± 2° C.) using a stereomicroscope. The OCC were washed 4 times through low bicarbonate-TALP (Parrish, et al. (1988), incorporated herein by reference, and placed into maturation plates (10 OCC per 50 ul drop). Maturation plates consist of ten 50 ul drops of maturation medium with estradiol-17B (1 ug/ml), FSH (0.5 ug/ml) and LH (0.5 ug/ml) (Sirard et al., 1988) in a 60 mm petri dish with 10 ml of paraffin oil.

Those oocytes not used as recipient oocytes were fertilized to provide donor embryos in subsequent experiments. Fertilization of oocytes was performed according to the procedure described in Sirard et al. (1988). Briefly, OCC were in vitro matured 22±2 hours, then washed 2 times through Sp-TALP (Parrish, et al., 1988) and moved into fertilization plates. Fertilization was performed in 60 mm plates with 10 drops (40 µl each) of fertilization medium (5 ml TL Stock-no glucose, 30 mg fatty-free BSA-6 mg/ml final, 50 µl pyruvate stock-0.2 mM final, 2.5 µl gentamicin-25 µg/ml final-optional) covered with oil and 10 OCC for each drop. The OCC were added, followed by $5 \times 10^4$ motile sperm, 0.2 ug of heparin, and 2 ul of PHE stock (20 µm penicillamine, 10 µm hypotaurine, 1 µm epinephrine, 21 µm sodium metabisulfate, and 118 µm DL-lactate syrup in 0.9% sodium chloride according to Leibfried and Bavister, 1982).

Motile sperm cells were prepared by the Percoll separation of frozen sperm procedure. A 45% percoll solution (3.090 ml/100 ml KCl, 2.920 ml/100 ml $NaH_2PO_4$, 4.675 g/100 ml NaCl, 2.380 g/100 ml HEPES, adjust the pH to 7.3) was prepared by a 1:1 dilution with 90% percoll using Sperm TL Stock Solution (SPTL) (2.10 mM $CaCl_2{}^2H_2O$, 3.1 mM KCl, 0.4 mM $MgCl_2 6H_2O$, 100 mM NaCl, 0.29 mM $NaH_2PO_4H_2O$, 21.6 mM Lactic Acid, 10 mM Hepes, 25 mM $NaHCO_3$, adjust pH to 7.4 before bringing to final volume; check osmolarity: 290–300 mOSM) according to Parrish, et al., 1988. The SPTL did not contain BSA. Two–three ml of 90% percoll was placed on the bottom of a conical tube (Falcon 2095). Two ml of 45% percoll was layered carefully on the top of the 90% percoll. The procedure was performed at room temperature. One unit of semen was thawed (35° C., 1 min.) and layered on top of the percoll gradients. The tube was centrifuged at 700×g for 30 min. The top layers were removed, and the concentrated motile sperm was available for use.

Following 44±2 hours after insemination, the OCC were stripped of cumulus cells, and the eggs were categorized as cleaved (≧2 cells) or uncleaved. The cleaved eggs were cultured in CR1-L-Glutamine medium for 3 to 5 days until they reach the morula or blastocyst stage.

Embryo Handling and Micromanipulation.

Recipient oocytes were enucleated by aspirating approximately one-eighth to one-fourth the cytoplasm juxtaposed to the polar body or the metaphase bulge using a 10–45 micron transfer pipette, leaving an enucleated membrane-bounded oocyte. Embryos were manipulated in calcium and magnesium-free TL Hepes buffered modified Tyrodes medium prepared according to Bavister et al., 1983. Nuclei from later stage donor embryos were removed by aspirating the nucleus and some surrounding membrane-bounded cytoplasm from a blastomere or by aspirating an entire blastomere. Micromanipulation was conducted using a holding pipette having an outer diameter of approximately 120–180 microns and an inner diameter of approximately 30 microns and a beveled, sharpened enucleation and transfer pipette having an outer diameter of approximately 10 to 45 microns. Whole blastomeres, containing nuclei, were removed from donor embryos and positioned in the perivitelline space of the recipient oocytes by the method of McGrath and Solter (1983).

Maintenance Procedures

Embryos were maintained in vitro in CR1-L-Glutamine medium for 6–18 hours prior to fusion. Zimmerman Cell Fusion Medium (GCA Corporation, Chicago, Ill.), was used for fusing donor and recipient cells. Cells from donor embryos were washed in the medium then placed in the fusion chamber with the Zimmerman medium. Following the fusion treatment, oocytes were placed in CR1-L-Glutamine medium, in 50 microliter drops, under paraffin oil in a humidified 5% $CO_2$ in air incubator and monitored for fusion and allowed to develop for five days.

Activation and fusion of the intact, membrane-bounded nuclei to the enucleated oocytes were carried out in Zimmerman Cell Fusion Medium by dielectrophoresis using a Zimmerman Electrofusion Instrument, GCA Corporation, Chicago, Ill. The fusion chamber consisted of two parallel electrodes 1 mm apart on a glass slide. The instrument was adjusted in the following manner:

Fusion voltage: 80–120 volts (DC)
Electrode distance: 1 mm
Alignment voltage: 1–5 volts (AC)
Alignment frequency: 1000 KHz
Pulse duration: 10–40 microseconds
Postfusion alignment time: 5 seconds
Number of Pulses: 1–6

Experiment

The experiment was designed to determine whether the development of nuclear transfer embryos (NTs) could be improved by maintaining the donor embryo cells and recipients in maintenance medium for an extended period of time. NTs were produced according to Prather et al. (1987) which is incorporated herein by reference. Specifically, in vitro matured oocytes were used as recipients, in vitro developed embryos were used as donors, and the subsequently formed NTs were developed in vitro in CR1 with 1 mM L-glutamine medium (CR1-L-GLN).

The treatment structure was a blocked one-way design with 3 treatments. Each donor embryo served as the block, i.e., every treatment was imposed on donor embryo cells from each donor embryo. Enucleation and transfer of donor blastomeres was performed at 24 hours post-oocyte aspiration. The three treatments were as follows: 1) fusion at 30 hours; 2) those that did not fuse at 30 hours and were then refused at 42 hours; and 3) fusion at 42 hours. During the manipulation process, the donor and recipient embryo cells were handled in calcium and magnesium free TALP-hepes. The cells were maintained in CR1-L-GLN during the waiting period before fusion as well as is the post-fusion development period. Embryos were developed in 50 microliter drops of this maintenance medium under paraffin oil in a humidified incubator with an atmosphere of 5% $CO_2$ in air. This experiment was replicated on three different days using three morula stage donor embryos (30–40 cells each) on each day of nuclear transfer. The results are illustrated in the following table:

| | Nuclear Transfer - Fusion at 30 Hours Versus 42 hours | | |
|---|---|---|---|
| FUSION | ACTIVATION | CLEAVAGE | DEVELOPMENT MORULA + BLASTOCYST[a] |
| 30 hr | | | |
| N 59/104 | 68/97 | 19/59 | 2/59 |
| % 56.9 | 71 | 32.0 | 4.7 ± 3.7[b] |
| 30/42 hr | | | |
| N 31/42 | | 19/31 | 7/31 |
| % 80.1 | | 63.9 | 22.2 ± 6.7[c] |
| 42 hr | | | |
| N 87/108 | 80/99 | 62/87 | 28/87 |
| % 80.4 | 81 | 71.0 | 32.6 ± 5.3[c] |

[a]: cultured 5 days in CR1 + L-Glutamine (1 Mm)
[b,c]: uncommon superscripts differ ($P < 0.05$)

The results indicate that when the fusion regime is changed to a later time period, i.e., following the maintenance period of this invention, development of NTs is similar to that of normal in vitro matured, fertilized and developed oocytes. Thus, the nuclear transfer embryo appears to have increased fusion and developmental rates when fusion is delayed by approximately 6–18 hours after the time fusion would normally take place, i.e., 34–48 hours after aspiration of the recipient oocytes.

It is understood that the invention is not confined to the particular construction and arrangement herein described, but embraces such modified forms thereof as come within the scope of the following claims.

BIBLIOGRAPHY

U.S. Pat. No. 4,994,384 to Prather et al.

U.S. Pat. No. 5,096,822 to Rosenkrans, Jr. et al.

Bavister et al., 1983, "Development of Preimplantation Embryos of the Golden Hamster in a Defined Culture Medium," *Biol. Reprod.*, 28: 235.

Bondioli, K.R. et al. 1990, "Production of Identical Bovine Offspring by Nuclear Transfer," *Theriogenology*, Vol. 13 (1): 165–174.

Briggs and King, 1952, "Transplantation of Living Nuclei from Blastula Cells into Enucleated Frogs' Eggs," *Zoology* 38:455–463.

Briggs, R., et al., 1964, "Transplantation of Nuclei of Various Cell Types from Neurulae of the Mexican Axolotl (*Ambystoma mexicanum*)," *Develop. Biol* 10: 233.

Comandon and de Fonbrune, 1939, "Greffe Nucleaire Totale, Simple ou Multiple, Chez une Amibe," *Soc. Biol.* 130:744.

Critzer, E. S. and N. L. First, 1986, "Use of Fluorescent Stain for Visualization of Nuclear Material in Living Oocytes and Early Embryos," *Stain Technology*, 61(1):1–5.

Eyestone, et al., 1987, "Culture of One- and Two-Cell Bovine Embryos to the Blastocyst Stage in the Ovine Oviduct" *Theriogenology*, 28:1–7.

Elsdale et al., 1960, "A Description of the Technique for Nuclear Transplantation in *Xenopus laevis*," *J. Embryol. Exp. Morph.*, 8(4):437–444.

First and Prather, 1991, "Genomic Potential in Mammals, " *Differentiation*, 48:1–8.

Graham, C. F., 1969, "The Fusion of Cells with One and Two Cell Mouse Embryos," *Wistar Inot. Symp. Monogr.*, 9:19.

Illmensee, K. and P. C. Hoppe, 1981, "Nuclear Transplantation in *Mus musculus:* Development Potential of Nuclei from Preimplantation Embryos, " *Cell* 23:9.

Kono, T., et al., 1991, "Development of Enucleated Mouse Oocytes Reconstituted with Embryonic Nuclei, " *J. Reprod. Fert.*, 93:165–172.

McGrath, J. and D. Solter, 1983, "Nuclear Transplantation in the Mouse Embryo by Microsurgery and Cell Fusion," *Science*, 220:1300.

McGrath, J. and D. Solter, 1984, "Inability of Mouse Blastomere Nuclei Transferred to Enucleated Zygotes to Support Development In Vitro," Science, 226:1317–1319, 1984.

Navara, C. S. et al., 1992, "Timing of Polarization in Bovine Embryos and Developmental Potential of Polarized Blastomeres, " (Abstract) *Proc Soc. Study Reprod.*, North Carolina State University (Jul. 12–15, 1992), p. 71.

Parrish, J.J. et al., 1988, "Capacitation of Bovine Sperm by Heparin," *Biol. Reprod.* 38, 1171–1180.

Prather, R.S. et al., 1987, *Biol. Reprod.*, 37:859–866.

Prather, R.S. et al., 1989, *Biol. Reprod.*, 41:414–418.

Robl, J.M. et al., 1986, "Nuclear Transplantation in Mouse Embryos: Assessment of Recipient Cell Stage," *Biol. Reprod.*, 34:733–739.

Sirard et al., 1988, *Biol. Reprod.*, 39:546–552.

Smith, L.C. and I. Wilmut, 1989, "Influence of Nuclear and Cytoplasmic Activity on the Development in vivo of Sheep Embryos after Nuclear Transplantation," *Biol. Reprod.*, 40:1027–1035.

Stice, S.L., and J.M. Robl, 1989, *Biol. Reprod.*, 39:657–664.

Surani, M.A.H. et al., 1986, "Nuclear Transplantation in the Mouse: Heritable Differences Between Paternal Genomes after Activation of the Embryonic Genome." *Cell*, 45:127–136.

Tsunoda, Y.. et al., 1987, *J. Exp. Zool.*, 242:147–151).

Willadsen, S.M., 1986, *Nature*, 320:63–65.

What is claimed is:

1. A method for producing cloned bovine embryos comprising the following steps:
   a. removing the chromosomal material from a metaphase II stage bovine oocyte to form an enucleated recipent oocyte;
   b. maintaining the enucleated recipient oocyte in CR-1+1 mM L-glutamine maintenance medium wherein the maintenance period is approximately 6 to 18 hours;
   c. placing a membrane bound nucleus from a donor 2–64 cell bovine embryo adjacent to the plasma membrane of the enucleated recipient oocyte and;
   d. inducing cell fusion between the membranes of the donor membrane-bound nucleus and the enucleated recipient oocyte to form an embryonic single cell with a nucleus from the donor, wherein the membranes are either electrically fused or fused with polyethylene glycol.

2. The method of claim 1 wherein the CR-1+1 mM L-glutamine maintenance media further comprises 5 mM hemicalcium L-lactage and 0.4 mM pyruvate.

3. The method of claim 1 further comprising, before step. d., orienting the donor membrane-bound nucleus and the enucleated recipient oocyte so that the plane of contact of their membranes is perpendicular to the direction of electric current flow.

* * * * *